(12) United States Patent
Buehring et al.

(10) Patent No.: US 7,541,030 B2
(45) Date of Patent: Jun. 2, 2009

(54) ANTIBODIES FOR IDENTIFYING AND/OR ISOLATING AT LEAST ONE CELL POPULATION WHICH IS SELECTED FROM THE GROUP COMPRISING HAEMATOPOIETIC STEM CELLS, NEURONAL STEM CELLS, NEURONAL PRECURSOR CELLS, MESENCHYMAL STEM CELLS AND MESENCHYMAL PRECURSOR CELLS

(75) Inventors: Hans-Joerg Buehring, Tuebingen (DE); Reiner Lammers, Tuebingen (DE); Selim Kuci, Tuebingen (DE); Tim Conze, Tuebingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 355 days.

(21) Appl. No.: 10/627,884

(22) Filed: Jul. 25, 2003

(65) Prior Publication Data

US 2004/0053343 A1 Mar. 18, 2004

(30) Foreign Application Priority Data

Sep. 4, 2002 (DE) ............................... 102 42 146

(51) Int. Cl.
*C07K 16/28* (2006.01)
*A61K 39/395* (2006.01)

(52) U.S. Cl. ............. 424/141.1; 424/143.1; 530/388.1; 530/388.22

(58) Field of Classification Search ........................ None
See application file for complete search history.

(56) References Cited

U.S. PATENT DOCUMENTS 6,245,898 B1 * 6/2001 Testa et al. ............. 530/388.85

FOREIGN PATENT DOCUMENTS

| EP | 1074617 | 2/2001 |
|---|---|---|
| WO | WO 00/06698 | 2/2000 |
| WO | WO 01/40466 | 6/2001 |
| WO | WO 01/54477 | 8/2001 |
| WO | WO 01/75067 | 10/2001 |
| WO | WO 02/04508 | 1/2002 |

OTHER PUBLICATIONS

Hooper et al., Oncogene, Mar. 27, 2003;22(12):1783-94.*
Rudikoff et al (Proc Natl Acad Sci USA 1982 vol. 79 p. 1979-1983.*
Casset et al. (2003) BBRC 307, 198-205.*
Conze, Tim et al., "CDCP1 is a novel marker for hematopoietic stem cells," Ann. N.Y. Acad. Sci. (2003), 996:222-226.
Scherl-Mostageer M., et al., "Identification of a novel gene, CDCP1, overexpressed in human colorectal cancer," Oncogene, (2001), 20: 4402-4408.
Yin, Amy H., et al. "AC133, a novel marker for human hematopoietic stem and progenitor cells" Blood, (1997) 90: 5002-5012.

* cited by examiner

*Primary Examiner*—David S Romeo
*Assistant Examiner*—Daniel C Gamett
(74) *Attorney, Agent, or Firm*—Knobbe, Martens Olson & Bear LLP

(57) ABSTRACT

The invention relates to monoclonal antibodies, or fragments thereof, for isolating and/or identifying at least one cell population which is selected from the group comprising haematopoietic stem cells, neuronal stem cells, neuronal progenitor cells, mesenchymal stem cells and mesenchymal progenitor cells. The antibodies, or fragments thereof, bind to an antigen which is the same as that bound by an antibody which is produced by the hybridoma cell lines CUB1, CUB2, CUB3 and CUB4, which were deposited in the DSMZ under the numbers DSM ACC2569, DSM ACC2566 and DSM ACC2565, on Aug, 14, 2002, and DSM ACC2551, on Dec. 7, 2002.

27 Claims, 3 Drawing Sheets

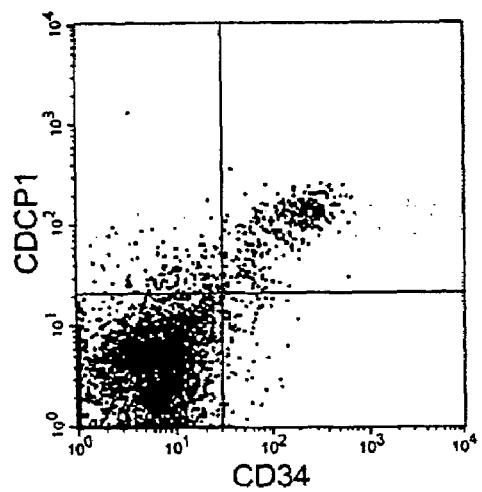 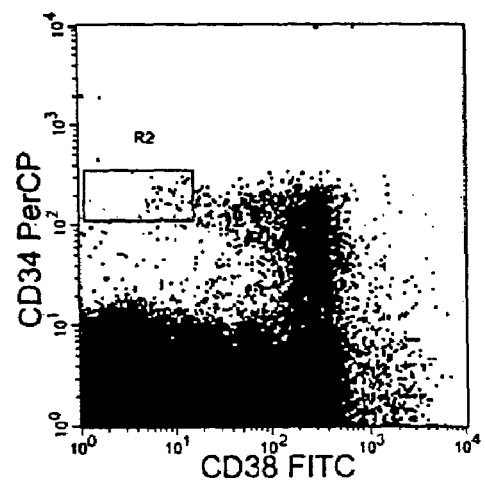
Fig. 2a  Fig. 2b
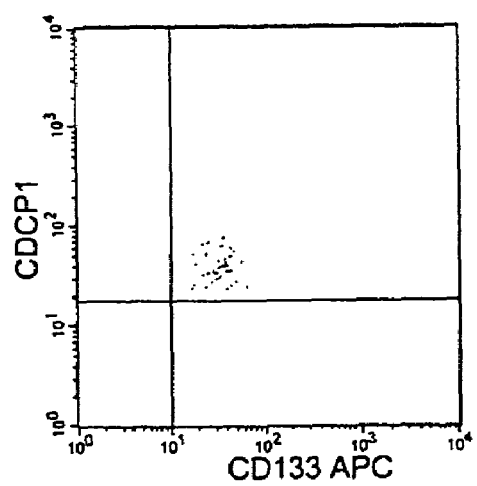
Fig. 2c

ANTIBODIES FOR IDENTIFYING AND/OR ISOLATING AT LEAST ONE CELL POPULATION WHICH IS SELECTED FROM THE GROUP COMPRISING HAEMATOPOIETIC STEM CELLS, NEURONAL STEM CELLS, NEURONAL PRECURSOR CELLS, MESENCHYMAL STEM CELLS AND MESENCHYMAL PRECURSOR CELLS

This Application claims the benefit of priority to the German Patent Application No. 102 42 146.3-44, filed Sep. 4, 2002, the disclosure of which is expressly incorporated herein by reference in its entirety.

BACKGROUND OF THE INVENTION

1. Field of the Invention

The present invention relates to a monoclonal antibody, or a fragment thereof, for isolating and/or identifying at least one cell population which is selected from the group comprising haematopoietic stem cells, neuronal stem cells, neuronal pre-cursor cells, mesenchymal stem cells and mesenchymal precursor cells.

The term "stem cell" denotes, in a general manner, any cell which has not yet differentiated and which possesses the ability both to produce identical descendants and to differentiate into specific developmental lines.

Adult stem cells have the function of maintaining cell number homeostasis in the tissue concerned, i.e. of replacing cells which have died. For this reason, stem cells are particularly to be found in tissues which are subjected to high stresses. Adult stem cells have been found in a very wide variety of tissues and organs, such as, for example, bone marrow, brain, liver, skin, intestine, cornea, etc.

In the bone marrow, haematopoietic stem cells produce new cells continuously since these latter cells are constantly required in the blood owing to the limited life span of most of the cells.

The starting point for the formation of blood cells is the pluripotent, undifferentiated haematopoietic stem cell which is still not determined for a specific function. When stem cells differentiate, precursor cells, which are unable to replicate themselves and only bring a specialized cell type to maturity, are formed first of all. Neither the pluripotent stem cell nor the different intermediate stages are able to fulfil cell-specific haematopoietic functions; it is only the cells which have matured which are able to do this. Progenitor cells which have entered upon a particular differentiation route then also keep to this route until maturation is achieved (commitment).

In addition to stem cells for haematopoietic cells, stem cell-like cells which are progenitors of nonhaematopoietic tissues are also present in the bone marrow. These progenitors of non-haematopoietic tissues were originally termed, inter alia, tissue culture plastic-adherent cells and have more recently been termed either mesenchymal stem cells or bone marrow stroma cells (MSCs).

These cells are of interest not only because of their multi-potency as regards differentiation; they are also of interest, for example, for their possible use in cell therapy and gene therapy.

The fact that, under certain conditions, mesenchymal stem cells can also differentiate into nerve cells means that, inter alia, there is a need to be able to distinguish these mesenchymal stem cells from neuronal progenitor cells.

These neuronal progenitor cells (termed NPCs below) are found in the central nervous system. They also express Nestin and are able to differentiate into neurones, astrocytes and oligodendrocytes.

Neuronal progenitor cells are CD133-positive; this cell surface marker was originally found on haematopoietic stem cells. However, it has recently been shown that this marker is also expressed by nervous tissue and skeletal muscle tissue. For these reasons, this marker is not suitable for distinguishing between different stem cells or progenitor cells on its own.

Since, as has been mentioned, haematopoietic stem cells continuously generate new cells in the bone marrow, stem cells coexist with the progenitor cells at the same time in the bone marrow. In the bone marrow, these cells are present in a complex arrangement, thereby making it difficult to identify rare cells. Stem cells and their direct descendants express a pheno-type which is virtually identical. For these reasons, it is not possible, either, to identify an ultimate stem cell simply on the basis of visible features.

The frequency of stem cells in the bone marrow is from $1\times10^{-5}$ to $1\times10^{-6}$. In addition, the stem cells are as a rule widely scattered in the given tissue, which means that they are difficult to detect.

As has been mentioned above, haematopoietic stem cells divide, under certain conditions, into progenitor cells whose further differentiation is to some degree already determined. Depending on the nature and quantity of the cytokines which are present, these myeloid and lymphoid progenitor cells can in turn generate a variety of other progenitor cells which are, however, no longer able to replicate themselves. Examples of cytokines which regulate haematopoiesis are granulocyte colony-stimulating factor (G-CSF), macrophage colony-stimulating factor (M-CSF), several interleukins, stem cell factor (SCF), erythropoietin (EPO), etc.

In order to investigate the haematopoietic (blood cell-forming) potential of stem cells, relevant human cell populations are transplanted into immunodeficient mice (NOD/SCID mice). If the transplanted cells are stem cells, it is then possible to detect human haematopoiesis in addition to the murine haematopoiesis. This in-vivo assay is used to characterize and identify stem cells by in fact analysing the progeny of individual cells.

2. Related Prior Art

As can be seen from the above, haematopoietic stem cells possess great therapeutic potential and are used in patients in whom the immune system is impaired or completely destroyed. FACS (fluorescence-activated cell sorter) can be used, for example, to 9-purify. haematopoietic stem cells from the bone marrow. This purification depends on the presence, on the stem cells, of particular cell surface proteins which distinguish the haematopoietic stem cells and the progenitor cells from other cell types and on the absence of other cell surface proteins, these latter proteins then being characteristic for differentiated haematopoietic cells. Each of the surface proteins binds a different monoclonal antibody, with each of these antibodies being conjugated to a different fluorescent dye, thereby making it possible to use FACS to separate the cells.

The cell surface marker CD34, in particular, has been used in the past for isolating haematopoietic stem cells.

In addition, antibodies directed against the antigen CD133 have recently been used for characterizing haematopoietic stem cells. Miraglia et al., "A novel five-transmembrane hematopoietic stem cell antigen: isolation, characterization and molecular cloning", Blood 90: 5013-5021, (1997) have shown that this antigen is a 120 kDa glycoprotein which possesses five transmembrane domains and which is expressed not only on haematopoietic stem cells and their progenitors but also on neuronal and endothelial stem cells.

CD133 antibodies are used, in addition to the conventional CD34 antibodies, for positively selecting haematopoietic stem cells and progenitor cells on a clinical scale. CD133 is only expressed on CD34$^{bright}$ (high fluorescence intensity) stem cells and progenitor cells. CD34$^{bright}$ CD133-positive cells are in the main negative for other erythroid progenitor cell markers such as CD36 and glycophorin A. In addition to stem cells which induced human haematopoiesis in: the NOD/SCID mouse model, the majority of granulocyte/macrophage progenitor cells have also been found in CD133-positive fractions derived from human bone marrow and peripheral blood.

SUMMARY OF THE INVENTION

In view of the above, it is an object of the present invention to provide a novel monoclonal antibody which can be used to selectively isolate and/or characterize particular cell populations, in particular haematopoietic stem cells and also neuronal and mesenchymal stem and progenitor cells.

According to the invention, this object is achieved by means of a monoclonal antibody, or a fragment thereof, with the antibody, or the fragment thereof, binding to the same antigen as does an antibody which is produced by the hybridoma cell lines as CUB1, CUB2, CUB3 and CUB4, which were deposited in the Deutsche Sammlung für Mikroorganismen und Zellkulturen [German collection of microorganisms and cell cultures] (DSMZ), in accordance with the Budapest treaty, under the numbers DSM ACC2569, DSM ACC2566 and DSM AC2565, on 14.08.2002, and DSM ACC2551, on 12.07.2002.

These deposits were made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by DSMZ under the terms of the Budapest Treaty, and subject to an agreement between Applicant and DSMZ which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited strains is not to be construed as a license to practice the invention in contravention of the rights granted under the authority of any government in accordance with its patent laws.

The object underlying the invention is fully achieved in this way.

The inventors were able to demonstrate, in their own experiments, that it is possible to use the novel antibodies according to the invention to isolate and characterize haematopoietic stem cells, mesenchymal stem cells and progenitor cells and neuronal stem cells and progenitor cells. In addition to this, the selectivity of the novel antibodies was found to be similar to that of an antibody directed against CD133.

One object of the invention relates, in particular, to monoclonal antibodies, or fragments thereof, which are produced by the hybridoma cell lines CUB1, CUB2, CUB3 and CUB4.

The inventors were surprisingly able to isolate the antibodies using the antigen CDCP1.

CDCP1 is a plasma membrane protein which possesses three potential "CUB" domains. These domains are immunoglobulin-like domains which are designated by the initial letters of the first three molecules possessing such domains which were identified. Proteins which possess these domains are known to be preferentially expressed in the embryonic stage and in early developmental stages.

The CDCP1 gene encoding this protein ("CUB domain-containing protein") has been described by Scherl-Mostageer et al., "Identification of a novel gene, CDCP1, overexpressed in human colorectal cancer", Oncogene 20: 4402-4408, (2001). This research group showed that this protein, or its mRNA, is strongly over-expressed in cancer types or tumours such as intestinal cancer and lung cancer. On the basis of its three-dimensional structure, it was identified as being a transmembrane protein which possessed three CUB domains in the extracellular domain, and the authors proposed that it was involved, in particular, in cell adhesion or interaction with the extracellular matrix (see Scherl-Mostageer et al.).

However, the possibility that this protein might also be expressed, in particular, on primitive haematopoietic stem cells in the bone marrow and peripheral blood and also on mesenchymal or neuronal stem cells and progenitor cells is neither reported nor suggested in this publication.

Instead of the antibody which is in each case mentioned, it is according to a further object also possible, within the context of the present invention, to use a fragment of the antibody without this in each case being expressly mentioned. In this connection, "fragment" is understood as meaning any fragment of the antibody which retains the antigen-binding function of the antibody. Examples of such fragments are $F_{ab}$, $F_{(ab')2}$, $F_v$ and other fragments such as CDR ("complementarity-determining region", hypervariable region) fragments. The said fragments exhibit the binding specificity of the antibody and can also be prepared recombinantly, for example using known methods.

The inventors were able to demonstrate that it is unexpectedly possible to use the antibodies which are directed against the plasma membrane protein CDCP1 to selectively characterize and isolate haematopoietic stem cells and mesenchymal and neuronal stem cells and progenitor cells.

When these novel antibodies were used to identify haematopoietic stem cells, it was found that the antibodies exhibited a selectivity which was superior to that of antibodies which are directed against CD34 and which is similar to that of the antibody which is directed against CD133.

For this reason, the novel antibodies, or fragments thereof, provide advantageous alternatives to the CD34 antibody when identifying or isolating haematopoietic stem cells.

Such monoclonal antibodies can be prepared using conventional methods (see Köhler and Milstein, "Continuous cultures of fused cells secreting antibody of predefined specifity", Nature 256:495-497, (1975)). According to this method, an animal is immunized with an antigen, the antibody-producing cells are isolated from the animal and these antibody-producing cells are fused with an immortal cell line. The resulting hybridoma cell lines are screened to determine whether they are able to produce an antibody against the antigen which was used for the immunization.

According to an object of the invention, the antibodies according to the invention also now make it possible to prepare further antibodies which bind to the same antigen. Using the antibodies according to the invention, it is possible to employ well known methods to isolate the corresponding antigen structures and to develop further monoclonal antibodies against the same antigen structures, with the known methods being employed in this case as well.

One object of the invention furthermore relates to hybridoma cell lines which are able to produce and release this type of antibody, in particular the hybridoma cell lines CUB1, CUB2, CUB3 and CUB4.

In providing the novel antibodies, the inventors have, for the first time, made available monoclonal antibodies, as well as hybridoma cell lines which produce and release these antibodies, which make it possible to selectively detect cell populations which are expressing the CDCP1 antigen. The antibodies therefore constitute a means, which is thus far unique and has many uses, for the physician and research worker to detect these types of cells, on the one hand, and, on the other hand, to manipulate these cells, where appropriate, either using the antibodies themselves or using reagents which are coupled to them.

Another object of the invention furthermore relates to a method for isolating and/or identifying at least one cell population which is selected from the group consisting of haematopoietic stem cells, neuronal stem cells, neuronal progenitor cells, mesenchymal stem cells and mesenchymal progenitor cells using an antibody, or a fragment thereof, with the antibody, or the fragment thereof, binding to the same antigen as does an antibody which is produced by the hybridoma cell lines CUB1, CUB2, CUB3 and CUB4, which were deposited in the DSMZ, in accordance with the Budapest treaty, under the numbers DSM ACC2569, DSM ACC2566 and DSM ACC2565, on 14.08.2002, and DSM ACC2551, on 12.07.2002.

In another embodiment and according to yet another object, the method according to the invention uses an antibody, or a fragment of an antibody, which is produced by the hybridoma cell lines CUB1, CUB2, CUB3 and CUB4.

Another object of the invention furthermore relates to a method for isolating and/or identifying at least one cell population, which is selected from the group consisting of haematopoietic stem cells, neuronal stem cells, neuronal progenitor cells, mesenchymal stem cells and mesenchymal progenitor cells, using an antibody, with the method comprising the following steps:

(a) bringing a sample of a cell suspension which contains at least one cell population into contact with the novel monoclonal antibody, or a fragment thereof, and (b) isolating and/or identifying the cells which are linked to the novel monoclonal antibody or to the fragment thereof.

Yet another object of the invention furthermore relates to a method for isolating and/or identifying at least one cell population, which is selected from the group consisting of haematopoietic stem cells, neuronal stem cells, neuronal progenitor cells, mesenchymal stem cells and mesenchymal progenitor cells, using an antibody, with the method comprising the following steps:

(a) bringing a sample of cell suspension which contains at least one cell population into contact with the novel monoclonal antibody, or a fragment thereof, and with at least one additional antibody which binds to at least one of the cell populations, and (b) isolating and/or identifying the cells which are linked to the monoclonal antibody, or to the fragment thereof, and to the additional antibody.

In this connection, the bringing into contact of a cell mixture with the antibody can according to a further object be effected in solution as is the case, for example, when using a flow cytometer (=fluorescence-activated cell sorter (FACS)).

Described in a general manner, cells are loaded, in flow cytometry, with antibodies which are on the one hand specific for a surface marker and on the other hand coupled to a fluorescent dye. The cells which are marker-positive fluoresce while the negative cells remain dark. It is therefore an object and possible to ascertain what proportion of a cell population is marker-positive. At the same time, a flow cytometer makes it possible to record the size and granularity of cells.

It is also an object and possible to use a method for magnetic cell separation (MACS, magnetic cell sorting). In this method, the cells are labelled with magnetic beads, with it being possible for these beads to be coupled to the antibodies, for example.

In addition, the bringing into contact can according to a further object also be carried out by immobilizing the monoclonal antibody on a support as is the case, for example, in column chromatography.

The cell suspension can according to one object be any solution containing bone marrow cells, blood cells or tissue cells.

After the cell suspension has been mixed with the antibody, the cells which are expressing the CDCP1 antigen bind the antibody, after which these cells can, in contrast to the cells which have not bound any antibody, be identified and/or isolated using the described methods.

In the method which was disclosed last, use is furthermore made of an additional antibody which also recognizes the cells. This antibody can according to one object, for example, be an antibody which is directed against the CD90 marker, in the case of neuronal progenitor cells, and be an anti-CD34 antibody, for example, in the case of haematopoietic cells. Using an additional antibody makes it possible to isolate/identify specific subpopulations, which consequently bind both the novel antibody and additional antibodies, in particular antibodies which are already known. This method can according to one object be used, for example, to characterize the cells more precisely with regard to their surface markers.

The cell populations which have been isolated by the methods can according to a further object then be used to repopulate, by means of transplantation, the bone marrow in immunosuppressed or immunodefective patients.

One object of the invention furthermore relates to the use of the novel antibodies, or fragments thereof, for isolating and/or identifying at least one cell population which is selected from the group consisting of haematopoietic stem cells, neuronal stem cells, neuronal progenitor cells, mesenchymal stem cells and mesenchymal progenitor cells.

According to yet another object, particular preference is given to using the novel antibodies, or fragments thereof, in connection with analysing patient samples, in particular tissue biopsies, bone marrow biopsies and/or blood samples, and in particular, when classifying leukaemias.

In the present instance, it has been possible to use the novel antibodies to detect expression of the corresponding antigen on leukaemia blasts as, for example, in the case of acute lymphatic leukaemia (ALL), acute myeloid leukaemia (AML) and chronic myeloid leukaemia (CML).

According to another object, the invention furthermore relates to the use of the CDCP-1 protein and/or of the nucleic acid which encodes the CDCP-1 protein for preparing antibodies, or fragments thereof, for isolating and/or identifying haematopoietic stem cells.

According to yet another object, the invention furthermore relates to a pharmaceutical composition which comprises at least one novel antibody, or fragments thereof.

In addition to the antibody, which represents the active compound in the composition, this composition can according to another object also comprise suitable buffers, diluents or additives. Suitable buffers include, for example, Tris-HCl, glycine and phosphate, while suitable diluents include, for example, aqueous solutions of NaCl, lactose or mannitol. Suitable additives include, for example, detergents, solvents, antioxidants and preservatives. A review of the substances which can be used for compositions of this nature is given, for example, in: A. Kibbe, "Handbook of Pharmaceutical Excipients", 3rd Ed., 2000, American Pharmaceutical Association and Pharmaceutical Press.

According to a further object, the invention furthermore relates to a kit which comprises at least one novel antibody, or fragments thereof.

Further advantages ensue from the enclosed figures and the description.

It will be understood that the features which are mentioned above, and those which are still to be explained below, can be used not only in the combination which is in each case specified but also on their own or with other combinations without departing from the scope of the present invention.

BRIEF DESCRIPTION OF THE DRAWINGS

Embodiments are depicted in the enclosed drawings and are explained in more detail in the description, in which:

FIG. 2a shows the coexpression of CD34 and CDCP1 on bone marrow cell populations (cells labelled with CD34-FITC) and CDCP1-PE (CUB 1));

FIG. 2b shows bone marrow cells in a CD34 versus CD38 plot and gating on the stem cell population (bone marrow cell pQpulations labelled with CD38-FITC, CDCP1-PE, CD34-PerCP and CD133-APC);

FIG. 2c shows the coexpression of CDCP1 and CD133 on CD34$^+$/CD38$^-$ bone marrow stem cells;

DETAILED DESCRIPTION

Preparing Transfectants

Starting with the cloning vector pBluescript II SK(+), into which the coding region of human CDCP1 had been cloned (obtained from Boehringer Ingelheim/Vienna), the coding sequence was subcloned into a pRK vector (PharMingen, San Diego, USA) and, at the same time, a five-fold myc-epitope (13 amino acids of the c-myc protein) was attached C-terminally. The pRK-CDCP1-myc5 DNA was cotransfected, together with a puromycin resistance plasmid (pSVpacAp: de la Luna et al., "Efficient transformation of mammalian cells with constructs containing a puromycin-resistance marker", Gene, 62(1): 121-126, 1988) into NIH-3T3 mouse cells using the CaCl$_2$ method.

After individual puromycin-resistant cells had been cloned, expression of the CDCDP1-myc5 protein in the transfected cells was detected by Western blotting using an anti-myc antiserum. The clone NIH-3T3/huCDCP1 was subsequently selected.

Immunization

Two Balb/c mice were immunized four times intraperitoneally with approx. 5–10×10$^6$ NIH-3T3/huCDCP1 cells using a standard protocol. Three to four days after the last immunization, the spleen was removed and the spleen cells were fused with SP2/0 myeloma cells using a standard protocol. The cell culture supernatants from growing, HAT-resistant hybridoma cells were tested by FACS analysis both on the transfectants and on the wild-type cell lines (NIH-3T3).

Supernatants which reacted selectively with the transfectants but not with the wild-type cell line NIH-3T3 were judged to be specific for CDCP1. The corresponding hybridoma cells were cloned (limiting dilution) and positive clones were selected. Four clones (CUB1, CUB2, CUB3 and CUB4) which reacted selectively with NIH-3T3/huCDCP1 cells were obtained (isotypes: one IgG2b [CUB1] and three IgG2a [CUB2-4]).

Figure 1A:
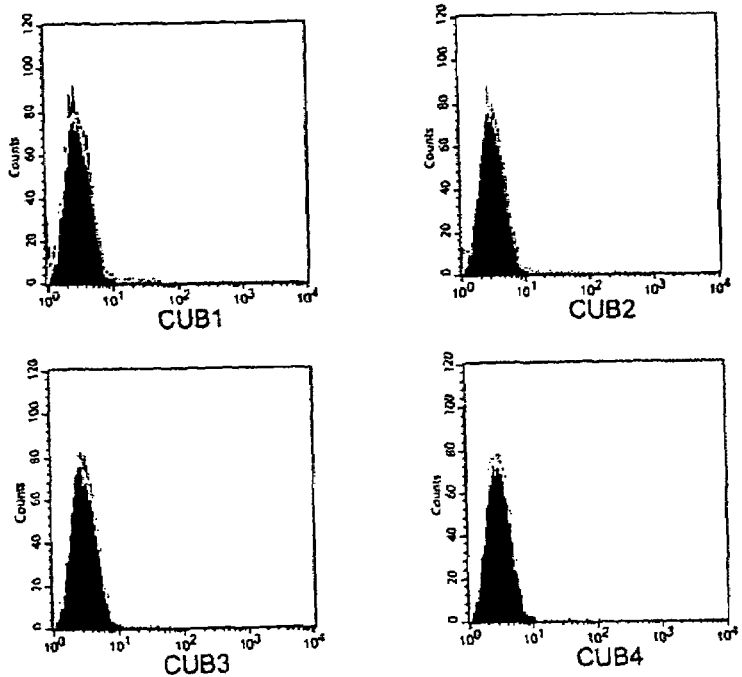
FIG. 1a shows the reactivity of the antibodies according to the invention with wild-type cells.
Figure 1B:
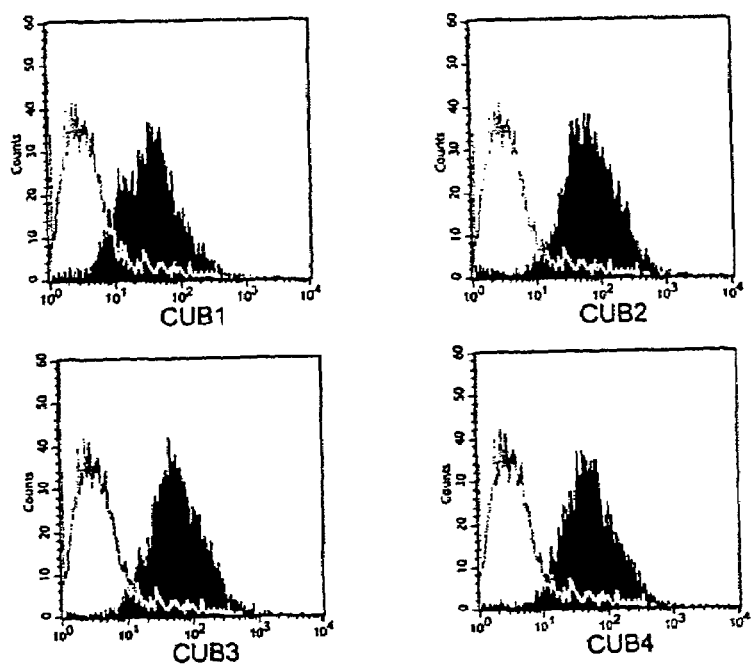
FIG. 1b shows the reactivity of the antibodies according to the invention with transfectants.

The histograms in FIG. 1a show that the four antibodies did not react with the wild-type cell. FIG. 1b shows histograms in which the reactivity of the four antibodies CUB1, CUB2, CUB3 and CUB4 with the transfectants is clearly depicted by the second, dark peak which is present in each case.

Investigating the Reactivity of the Antibodies on Peripheral Blood Cells

The reactivity of the antibodies on peripheral blood cells was tested first of all. The results of these investigations are shown in Table 1 below.

It was found that CD3$^+$ T lymphocytes, CD20$^+$ B lymphocytes, CD56$^+$ NK cells, CD14$^+$ monocytes, neutrophilic granulocytes, Siglec-8$^+$ eosinophilic granulocytes, CD235a$^+$ erythrocytes and CD61$^+$ platelets were negative for CDCP1.

TABLE 1

Reactivity of the CDCP1-specific antibody CUB1 on peripheral blood cells

| Cell type | Reactivity |
|---|---|
| T lymphocytes (CD3$^+$) | — |
| B lymphocytes (CD20$^+$) | — |
| NK cells (CD56$^+$) | — |
| Monocytes (CD14$^+$) | — |
| Neutrophilic granulocytes (CD15$^+$) | — |
| Eosinophilic granulocytes (Siglec-8$^+$) | — |
| Basophilic granulocytes (CD203c$^+$) | — |
| Erythrocytes (CD235a$^+$) | — |
| Platelets (CD61$^+$) | — |

The results of the reactivity of the antibodies on various cell lines, which are listed horizontally, are shown in Table 2 below. The four antibodies tested, i.e. CUB1 to CUB4, are listed vertically.

(Description of the Cell Lines:

K-562: erythroleukaemia; WERI-RB-1: retinoblastoma; BV-173: Pro-B cell leukaemia; HEL: erythroleukaemia; HL-60: promyelocytic leukaemia; KU-812: basophilic leukaemia; HepG2: hepatocellular carcinoma; MOLT-4: T-lymphocytic leukaemia).

TABLE 2

Reactivity of the CDCP1-specific antibodies CUB1, CUB2, CUB3 and CUB4 on various cell lines

|  | CD34-Tf* | CD133-Tf* | K-562 | WERI-RB-1 | BV-173 | HEL | HL-60 | KU-812 | Hep-G2 | MOLT-4 |
|---|---|---|---|---|---|---|---|---|---|---|
| CUB1 | − | − | + | − | − | − | − | − | − | − |
| CUB2 | − | − | + | − | − | − | − | − | − | − |
| CUB3 | − | − | + | − | − | − | − | − | − | − |
| CUB4 | − | − | + | − | − | − | − | − | − | − |

*Tf = Transfectant

It was found that all the cell lines tested were negative for CDCP1 apart from K-562. Scherl-Mostageer et al. have already shown that K-562, an erythroleukaemic cell line, expresses CDCP1 mRNA.

Further investigations were carried out into the correlated expression of CDCP1 and the other stem-cell markers CD34 and CD133 on various subsets of leukaemia blasts. The results obtained in these investigations are summarized in Table 3 below. The expression patterns were obtained by means of standard immunofluorescence labellings, using the antibodies, and then carrying out FACS analysis.

The analysis showed that CDCP1 is an independent marker in relation to the other stem cell markers since its expression is not necessarily correlated with that of the other markers. Frequent coexpression of all three stem cell markers can be seen, in particular, in the case of the myeloid leukaemias (AML and CML).

TABLE 3

Expression of CDCP1 on leukaemia blasts

|  | ALL (B-ALL,, Pro-B-ALL, Pre-B-ALL, C-ALL | AML (M1-M5) | CML (Blast crisis) |
|---|---|---|---|
| CD34+CD133+CDCP1+ | 2/20 | 4/11 | 4/10 |
| CD34+CD133+CDCP1− | 5/20 | 2/11 | 0/10 |
| CD34+CD133−CDCP1+ | 1/20 | 1/11 | 2/10 |
| CD34+CD133−CDCP1− | 7/20 | 0/11 | 2/10 |
| CD34−CD133+CDCP1+ | 0/20 | 2/11 | 0/10 |
| CD34−CD133+CDCP1− | 0/20 | 0/11 | 0/10 |
| CD34−CD133−CDCP1+ | 1/20 | 0/11 | 1/10 |
| CD34−CD133−CDCP1− | 4/20 | 2/11 | 1/10 |

In the table, ALL denotes acute lymphatic leukaemia while AML denotes acute myeloid leukaemia and CML denotes chronic myeloid leukaemia (the additional designations are classification and characterization designations which are customarily used for the acute leukaemias).

The novel antibodies can consequently be used, for example, in routine diagnoses in connection with leukaemias.

Investigating the Reactivity of the Antibodies on Bone Marrow Cells

The reactivity of the antibodies with bone marrow cell populations was subsequently investigated. It turned out that CDCP1 is exclusively expressed on CD34+ stem cells and not on other populations (see FIG. 2a). The FACS-sorted CDCP1+ fraction consisted almost entirely of immature blasts and immature colonies: CFU-GM (colony-forming unit granulocyte macrophage), BFU-E (burst-forming unit erythroid) CFU-GEMM (colony-forming unit granulocyte-erythroid-macrophage-megakaryocyte).

FIGS. 2b and 2c show the results of a four-colour analysis of bone marrow cells.

In order to carry out the four-colour analysis, the cells were labelled with the following antibody conjugates: CUB1-PE (phycoerythrin), CD133-APC (allophycocyanin), CD38-FITC (fluorescein isothiocyanate) and CD34-PerCP (peridin chlorophyll A protein).

In the plot in FIG. 2b, CD34 is plotted against CD38. Stem cells are found in the rare CD34+/CD38− fraction (Terstappen and Huang "Analysis of bone marrow stem cell", Blood Cells 20(1): 45-61, 1994). In the plot in FIG. 2b, this population is shown in the "R2-region".

In the plot in FIG. 2c, CDCP1 is plotted against CD133. This plot depicts the cells which can be seen in the "R2" region in the plot in FIG. 2b. FIG. 2c shows that essentially all the CD34+/CD38− stem cells coexpress CDCP1 and CD133.

In other experiments, the inventors were able to demonstrate that, 6 weeks after CDCP1-positive cells had been transplanted into NOD/SCID mice, human CD45+ cells had formed in the bone marrow of the mice. (CD45+ is a marker for haematopoietic cells). This consequently proves that the cells which are isolated using the novel antibodies are able to carry out haematopoiesis.

Investigating the Reactivity of the Antibodies on Neuronal and Mesenchymal Stem Cells In other experiments, the reactivity of the antibodies towards neuronal and mesenchymal stem cells was investigated.

Commercially available foetal neuronal progenitor cells (in the following NPC) and mesenchymal stem cells, obtained from Cell-Systems, St. Katharinen, Germany, were used for this purpose.

Figure 3:
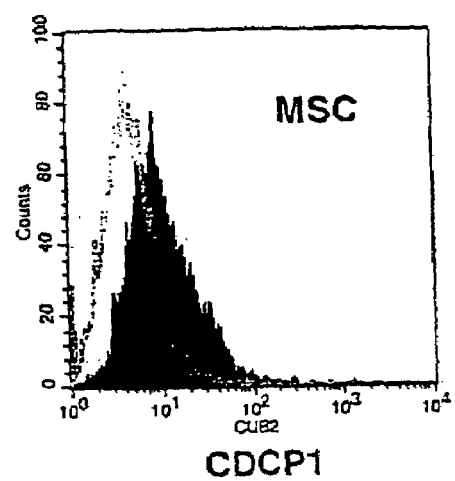
FIG. 3 shows the expression of CDCP1 on mesenchymal stem cells.
Figure 4A:
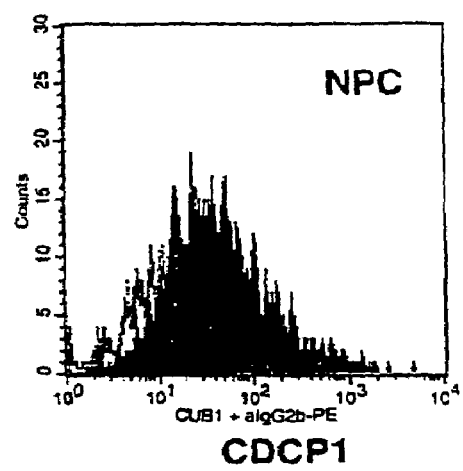
FIG. 4a shows the expression of CDCP1 on neuronal stem cells.

In FIG. 3, the second dark peak in the histogram shows that the CUB2 antibody reacts with mesenchymal stem cells. The histogram in FIG. 4a shows the reactivity with NPC, with the antibody CUB2 in this case being labelled with PE (phycoerythrin).

In order to carry out the coexpression analysis, the cells were labelled with the following antibody conjugates: CUB1+alqG2bPE (phycoerythrin), and CD90-APC (allophycocyanin). CD90 is known to be expressed on NPC (see, for example Vogel et al., "Heterogeneity among human bone marrow-derived mesenchymal stem cells and neural progenitor cells", Haematologica 88: 126-133, (2003)).

Figure 4B:
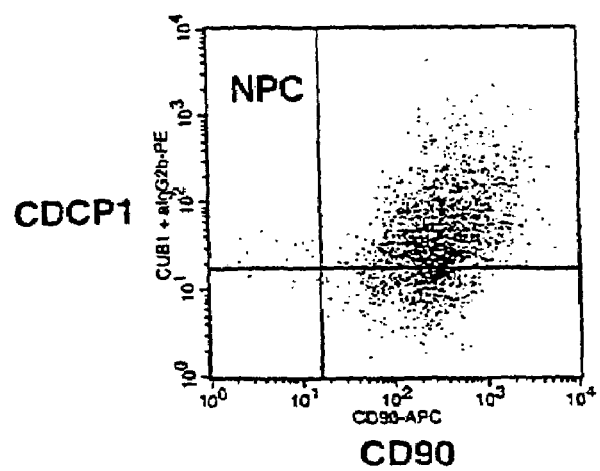
FIG. 4b shows the coexpression of CDCP1 and CD90 on neuronal stem cells.

In the plot in FIG. 4b, CDCP1 is plotted against CD90. It can be seen that the majority of the NPC cells expressed CDCP1 (in addition to CD90 as the "confirmation marker").

In summary, therefore, these data show that CDCP1 is a novel marker for haematopoietic stem cells and for mesenchymal or neuronal stem cells/progenitor cells. It is possible to use the antibody according to the invention which is directed against this marker to select CDCP1-expressing stem cells in a simple manner and then, for example, transplant them for the purpose of repopulating. The antibody according to the invention is consequently of very great importance for selecting haematopoietic or mesenchymal and/or neuronal stem cells. In addition, it constitutes an outstanding alternative to the CD133 and CD34 markers which are commonly used for selecting stem cells.

Therefore, what we claim is:

1. Monoclonal antibody, wherein the antibody binds to an epitope of CUB domain-containing protein 1 (CDCP 1) which is the same as that bound by an antibody which is produced by the hybridoma cell lines CUB1, CUB2, CUB3 or CUB4, which were deposited in the Deutsche Sammlung für Mikroorganismen und Zellkulturen (DSMZ), in accordance with the Budapest treaty, under the numbers DSM ACC2569, DSM ACC2566 and DSM ACC2565, on Aug. 14, 2002, and DSM ACC2551, on Jul. 12, 2002.

2. Monoclonal antibody, which is produced by the hybridoma cell line CUB1, which is deposited in the DSMZ under the number DSM ACC2569.

3. Monoclonal antibody, which is produced by the hybridoma cell line CUB2, which is deposited in the DSMZ under the number DSM ACC2566.

4. Monoclonal antibody, which is produced by the hybridoma cell line CUB3, which is deposited in the DSMZ under the number DSM ACC2565.

5. Monoclonal antibody, which is produced by the hybridoma cell line CUB4, which is deposited in the DSMZ under the number DSM ACC2551.

6. Hybridoma cell line, which produces an antibody according to claim 2.

7. Hybridoma cell line, which produces an antibody according to claim 3.

8. Hybridoma cell line, which produces an antibody according to claim 4.

9. Hybridoma cell line, which produces an antibody according to claim 5.

10. Pharmaceutical composition comprising at least one monoclonal antibody according to claim 1.

11. Pharmaceutical composition comprising at least one monoclonal antibody according to claim 2.

12. Pharmaceutical composition comprising at least one monoclonal antibody according to claim 3.

13. Pharmaceutical composition comprising at least one monoclonal antibody according to claim 4.

14. Pharmaceutical composition comprising at least one monoclonal antibody according to claim 5.

15. Kit, comprising at least one monoclonal antibody according to claim 1.

16. Kit, comprising at least one monoclonal antibody according to claim 2.

17. Kit, comprising at least one monoclonal antibody according to claim 3.

18. Kit, comprising at least one monoclonal antibody according to claim 4.

19. Kit, comprising at least one monoclonal antibody according to claim 5.

20. A fragment of a monoclonal antibody produced by the hybridoma cell line CUB1, which is deposited in the DSMZ under the number DSM ACC2569, wherein said fragment is selected from the group consisting of Fab, F(ab')2', Fv and a fragment comprising complementary-determining regions (CDRs), and wherein said fragment retains antigen-binding specificity of said antibody.

21. A fragment of a monoclonal antibody produced by the hybridoma cell line CUB2, which is deposited in the DSMS under the number DSM ACC2566, wherein said fragment is selected from the group consisting of Fab, F(ab')2', Fv and a fragment comprising complementary-determining regions (CDRs), and wherein said fragment retains antigen-binding specificity of said antibody.

22. A fragment of a monoclonal antibody produced by the hybridoma cell line CUB3, which is deposited in the DSMZ under the number DSM ACC2565, wherein said fragment is selected from the group consisting of Fab, F(ab')2', Fv and a fragment comprising complementary-determining regions (CDRs), and wherein said fragment retains antigen-binding specificity of said antibody.

23. A fragment of a monoclonal antibody produced by the hybridoma cell line CUB4, which is deposited in the DSMZ under the number DSM ACC2551, wherein said fragment is selected from the group consisting of Fab, F(ab')2', Fv and a fragment comprising complementary-determining regions (CDRs), and wherein said fragment retains antigen-binding specificity of said antibody.

24. A pharmaceutical composition comprising the fragment of claim 20.

25. A pharmaceutical composition comprising the fragment of claim 21.

26. A pharmaceutical composition comprising the fragment of claim 22.

27. A pharmaceutical composition comprising the fragment of claim 23.

* * * * *

UNITED STATES PATENT AND TRADEMARK OFFICE
CERTIFICATE OF CORRECTION

PATENT NO. : 7,541,030 B2  
APPLICATION NO. : 10/627884  
DATED : June 2, 2009  
INVENTOR(S) : Buehring et al.

It is certified that error appears in the above-identified patent and that said Letters Patent is hereby corrected as shown below:

Column 1, line 10, after the title, please insert the header --Foreign Application Priority Data--.
Column 1, line 59, please delete "stroma" and insert therefore, --stromal--.
Column 2, line 48, please delete "9-purify." and insert therefore, --purify--.
Column 3, line 10, please delete "in:" and insert therefore, --in--.
Column 4, lines 54-55, please delete "specifity"," and insert therefore, --specificity",--.
Column 6, line 54, please delete "and" and insert therefore, --and,--.
Column 7, line 38, please delete "pQpulations" and insert therefore, --populations--.
Column 7, line 61, please delete "(pSVpacAp:" and insert therefore, --(pSVpacΔp:--.
Column 7, line 67, please delete "CDCDP1" and insert therefore, --CDCP1--.
Column 10, line 55, please delete "+alqG2bPE" and insert therefore, --+algG2bPE--.
Column 10, line 55, please delete "phycoerythrin)," and insert therefore, --phycoerythrin)--.
Claim 1, line 5, please delete "(CDCP 1)" and insert therefore, --(CDCP1)--.
Claim 28, line 3, please delete "Fab, F(ab')2', Fv" and insert therefore, --$F_{ab}$, $F_{(ab')2'}$, $F_v$--.
Claim 29, line 2, please delete "DSMS" and insert therefore, --DSMZ--.
Claim 29, line 3, please delete "Fab, F(ab')2', Fv" and insert therefore, --$F_{ab}$, $F_{(ab')2'}$, $F_v$--.
Claim 30, line 3, please delete "Fab, F(ab')2', Fv" and insert therefore, --$F_{ab}$, $F_{(ab')2'}$, $F_v$--.
Claim 31, line 1, please delete "Fab, F(ab')2', Fv" and insert therefore, --$F_{ab}$, $F_{(ab')2'}$, $F_v$--.

Signed and Sealed this

Ninth Day of February, 2010

David J. Kappos  
*Director of the United States Patent and Trademark Office*

UNITED STATES PATENT AND TRADEMARK OFFICE
CERTIFICATE OF CORRECTION

PATENT NO.        : 7,541,030 B2                                                        Page 1 of 1
APPLICATION NO.   : 10/627884
DATED             : June 2, 2009
INVENTOR(S)       : Buehring et al.

It is certified that error appears in the above-identified patent and that said Letters Patent is hereby corrected as shown below:

Column 1, line 10, after the title, please insert the header --Foreign Application Priority Data--.
Column 1, line 59, please delete "stroma" and insert therefore, --stromal--.
Column 2, line 48, please delete "9-purify." and insert therefore, --purify--.
Column 3, line 10, please delete "in:" and insert therefore, --in--.
Column 4, lines 54-55, please delete "specifity"," and insert therefore, --specificity",--.
Column 6, line 54, please delete "and" and insert therefore, --and,--.
Column 7, line 38, please delete "pQpulations" and insert therefore, --populations--.
Column 7, line 61, please delete "(pSVpacAp:" and insert therefore, --(pSVpacΔp:--.
Column 7, line 67, please delete "CDCDP1" and insert therefore, --CDCP1--.
Column 10, line 55, please delete "+alqG2bPE" and insert therefore, --+algG2bPE--.
Column 10, line 55, please delete "phycoerythrin)," and insert therefore, --phycoerythrin)--.
Column 11, Claim 1, line 10, please delete "(CDCP 1)" and insert therefore, --(CDCP1)--.
Column 12, Claim 20, line 14, please delete "Fab, F(ab')2', Fv" and insert therefore, --$F_{ab}$, $F_{(ab')2'}$, $F_v$--.
Column 12, Claim 21, line 19, please delete "DSMS" and insert therefore, --DSMZ--.
Column 12, Claim 21, line 21, please delete "Fab, F(ab')2', Fv" and insert therefore, --$F_{ab}$, $F_{(ab')2'}$, $F_v$--.
Column 12, Claim 22, line 28, please delete "Fab, F(ab')2', Fv" and insert therefore, --$F_{ab}$, $F_{(ab')2'}$, $F_v$--.
Column 12, Claim 23, line 35, please delete "Fab, F(ab')2', Fv" and insert therefore, --$F_{ab}$, $F_{(ab')2'}$, $F_v$--.

This certificate supersedes the Certificate of Correction issued February 9, 2010.

Signed and Sealed this

Ninth Day of March, 2010

David J. Kappos
*Director of the United States Patent and Trademark Office*